(12) United States Patent
Adams

(10) Patent No.: US 8,585,699 B2
(45) Date of Patent: *Nov. 19, 2013

(54) SPHINCTEROTOME WITH IMPROVED ORIENTATION

(75) Inventor: Mark L. Adams, Sandy, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/290,480

(22) Filed: Nov. 7, 2011

(65) Prior Publication Data

US 2012/0053607 A1 Mar. 1, 2012

Related U.S. Application Data

(63) Continuation of application No. 12/245,884, filed on Oct. 6, 2008, now Pat. No. 8,066,703.

(60) Provisional application No. 60/978,336, filed on Oct. 8, 2007.

(51) Int. Cl.
*A61B 18/18* (2006.01)

(52) U.S. Cl.
USPC .............................................. 606/47; 604/22

(58) Field of Classification Search
USPC ......... 606/47, 167, 170, 79; 604/22; 600/104, 600/105
See application file for complete search history.

(56) References Cited

U.S. PATENT DOCUMENTS

| | | | |
|---|---|---|---|
| 4,846,175 A | 7/1989 | Frimberger | |
| 5,024,617 A | 6/1991 | Karpiel | |
| 5,035,696 A * | 7/1991 | Rydell | ............................ 606/47 |
| 5,075,062 A | 12/1991 | Karpiel | |
| 5,547,469 A | 8/1996 | Rowland et al. | |
| 5,810,807 A | 9/1998 | Ganz et al. | |
| 5,868,698 A | 2/1999 | Rowland et al. | |
| 5,984,920 A | 11/1999 | Steinbach | |
| 6,017,340 A | 1/2000 | Cassidy et al. | |
| 6,450,948 B1 | 9/2002 | Matsuura et al. | |
| 6,579,300 B2 | 6/2003 | Griego et al. | |
| 6,676,659 B2 | 1/2004 | Hutchins et al. | |
| 6,766,720 B1 | 7/2004 | Jacobsen et al. | |
| 6,827,718 B2 | 12/2004 | Hutchins et al. | |
| 7,878,984 B2 * | 2/2011 | Jacobsen et al. | ............... 600/585 |
| 8,066,703 B2 * | 11/2011 | Adams | ............................ 606/47 |
| 2002/0049423 A1 | 4/2002 | Howell et al. | |
| 2004/0111044 A1 | 6/2004 | Davis et al. | |
| 2004/0181136 A1 | 9/2004 | McDaniel et al. | |
| 2004/0181174 A2 | 9/2004 | Davis et al. | |
| 2004/0243056 A1 | 12/2004 | Rowland et al. | |
| 2005/0070721 A1 | 3/2005 | Bae et al. | |
| 2005/0070821 A1 | 3/2005 | Deal et al. | |
| 2007/0135763 A1 | 6/2007 | Musbach et al. | |

FOREIGN PATENT DOCUMENTS

DE 33 47 122 6/1985

* cited by examiner

*Primary Examiner* — Victor Nguyen

(74) *Attorney, Agent, or Firm* — Seager, Tufte & Wickhem LLC

(57) ABSTRACT

A sphincterotome including a cutting wire may be configured such that, when activated, the cutting wire assumes a desired cutting position at or near the "12 o'clock" position or any other desired angular configuration. A sphincterotome may have controlled bending characteristics. A distally located micromachined hypotube may, in some instances, provide desired bending characteristics to a sphincterotome.

10 Claims, 4 Drawing Sheets

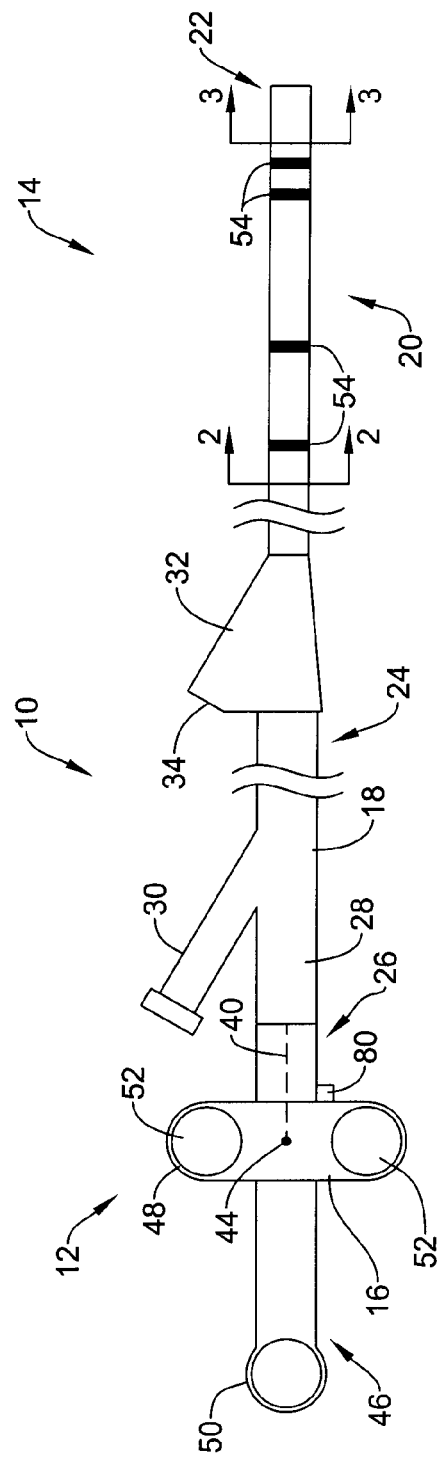
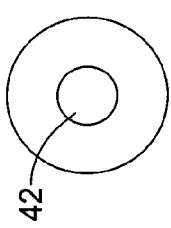
Figure 3
Figure 2
Figure 1

SPHINCTEROTOME WITH IMPROVED ORIENTATION

RELATED APPLICATIONS

This application is a continuation of U.S. patent application Ser. No. 12/245,884, filed Oct. 6, 2008, which claims the benefit of U.S. Provisional Application No. 60/978,336, filed Oct. 8, 2007, the entire disclosures of which are incorporated herein by reference.

TECHNICAL FIELD

The present invention pertains generally to medical devices and more particularly to medical devices such as sphincterotomes.

BACKGROUND

In procedures such as endoscopic sphincterotomy, a sphincterotome may be used in conjunction with an endoscope to provide surgical cutting inside of a patient. Exemplary sphincterotomes are disclosed in commonly assigned U.S. Pat. Nos. 5,547,469 and 5,868,698 to Rowland et al., the disclosures of which are incorporated herein by reference. The sphincterotome may, for example, be used to partially cut open the sphincter muscle for treatment such as removal of common bile duct stones forming an obstruction. A sphincterotome may include a cutting wire that can be activated by bending the sphincterotome, thereby permitting the cutting wire to extend from the sphincterotome.

However, when activating the cutting wire, it may be difficult to control the exact positioning of the cutting wire. In some instances, it may be desirable to position the activated cutting wire in an angular configuration commonly referred to in the art as the "12 o'clock" position, or in any other desirable angular configuration.

There remains a need, therefore, for an improved sphincterotome that is configured such that, when activated, the cutting wire assumes a desired cutting position at or near the "12 o'clock" position, or any other desired angular configuration. A need remains for an improved sphincterotome with controlled bending characteristics.

SUMMARY

The invention pertains to an improved sphincterotome that is configured such that, when activated, the cutting wire assumes a desired cutting position at or near the "12 o'clock" position or any other desired angular configuration. In some cases, activating the cutting wire may include application of an electrical current, but this is not required. The invention pertains to an improved sphincterotome having controlled bending characteristics.

Accordingly, an illustrative but non-limiting example of the invention may be found in a sphincterotome having an elongate shaft and a cutting element lumen extending through the elongate shaft. A micromachined hypotube may be disposed within a distal region of the elongate shaft. A cutting element may be disposed within the cutting element lumen such that an exposed portion of the cutting element is disposed exterior to the micromachined hypotube.

Another illustrative but non-limiting example of the invention may be found in a sphincterotome that is movable between a cutting position and a non-cutting position. The sphincterotome includes an elongate shaft that defines a cutting wire lumen extending within the elongate shaft. A cutting wire may be disposed within the cutting wire lumen. The sphincterotome includes apparatus or structure disposed exterior to the elongate shaft that is configured to limit a bending plane of the elongate shaft.

Another illustrative but non-limiting example of the invention may be found in a sphincterotome that has an elongate shaft that defines a cutting wire lumen. A cutting wire may be disposed within the cutting wire lumen. A distal region of the elongate shaft may be configured to have a greater flexibility in an activating bending plane and a lesser flexibility in an orthogonal bending plane.

The above summary of the present invention is not intended to describe each disclosed embodiment or every implementation of the present invention. The Figures, Detailed Description and Examples which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 1 is a view of a sphincterotome in accordance with an illustrative but non-limiting example of the invention;

FIG. 2 is a cross-sectional view taken along line 2-2 of FIG. 1;

FIG. 3 is a cross-sectional view taken along line 3-3 of FIG. 1;

Figure 4:
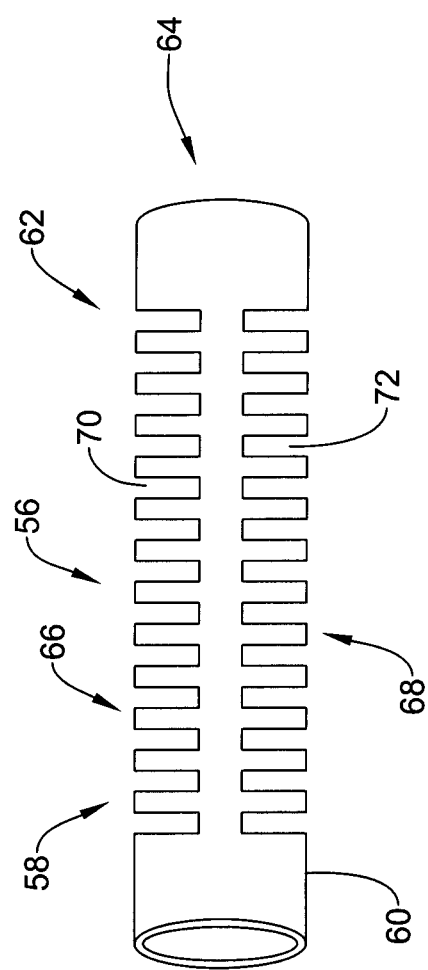
FIG. 4 is a view of a micromachined hypotube that may be incorporated into the sphincterotome of FIG. 1, in accordance with an illustrative but non-limiting example of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

The present invention generally pertains to a sphincterotome 10, as illustrated in FIG. 1. The sphincterotome 10 can be seen as including a proximal section 12 and a distal section 14. A handle 16 is disposed within the proximal section 12 and an elongate shaft 18 extends distally therefrom. The handle 16 may be formed of any suitable metallic or polymeric material, such as those discussed hereinafter. The elongate shaft 18 itself has a distal region 20 defining a distal end 22 and a proximal region 24 defining a proximal end 26. In some instances, it is contemplated that part of the elongate shaft 18 may undergo processing that may impart a curve or bias thereto, although this is not required. The elongate shaft 18 may be formed of or include any suitable polymeric material. In some cases, the elongate shaft 18 may include portions made from or including polytetrafluoroethylene, better known as TEFLON®.

A hub 26 may be disposed within the proximal region 24 of the elongate shaft 18. In some instances, if desired, the hub 26 may include a first hub portion 28 having a side port 30 that may be used to gain fluid access to an interior of the elongate shaft 18. The hub 26 may also include a second hub portion 32 that may, if desired, provide guidewire access to the interior of the elongate shaft 18 via a guidewire port 34 that is provided within the second hub portion 32. The elongate shaft 18 can be seen as extending distally to a distal end 22 of the elongate shaft 18. The elongate shaft 18 may be considered as including the hub 26, first hub portion 28 and second hub portion 32. The hub 26 and defined portions thereof may be formed of any suitable polymeric material.

As noted, the elongate shaft 18 includes an interior. FIGS. 2 and 3, which are cross-sections taken through the elongate shaft 18, provide illustrative but non-limiting examples of an interior of the elongate shaft 18. In FIG. 2, which is taken through a relatively proximal portion of the elongate shaft 18, it can be seen that the elongate shaft includes a first lumen 36 and a second lumen 38. In some instances, the elongate shaft 18 may include only one lumen, or may include three or more lumens.

In the illustrated embodiment, the first lumen 36 may, for example, be a guidewire lumen in communication with the guidewire port 34 disposed within hub 32. The second lumen 38 may, if desired, accommodate a cutting element 40. The cutting element 40 may extend from the handle 16 to a position within the distal region 20 of the elongate shaft 18. In some instances, the cutting element 40 may be a cutting wire, as known in the art. In some cases, the cutting element 40 may be a stranded or braided wire.

FIG. 3 is a cross-section taken through a relatively distal portion of the elongate shaft 18. In this view, only a single lumen 42 is present. In some cases, the first lumen 36 and the second lumen 38 may merge into a single lumen 42. In some cases, the second lumen 38 (through which the cutting element 40 is disposed) may terminate at a position proximal of where this cross-section is taken as the cutting element 40 itself may extend external to the shaft or terminate proximal of the cross-section point. In other cases, the elongate shaft 18 may include one, two, three or more lumens that extend all the way to the distal end 22 of the elongate shaft 18. In some cases, the elongate shaft 18 may be configured to provide rapid exchange capability and thus may include a short guidewire lumen (not illustrated) extending through a distal portion of the elongate shaft 18.

Returning to FIG. 1, it should be noted that the cutting element 40 (seen in FIG. 2) has a distal end (discussed later with respect to FIGS. 5 and 6) and a proximal end 44. In some cases, the proximal end 44 may be secured to the handle 16. More particularly, the handle 16 may include a stationary portion 46 and a movable portion 48. The stationary portion 46 may be secured to the elongate shaft 18 while the proximal end 44 of the cutting element 40 may be secured to the movable portion 48. The movable portion 48 may be slidingly disposed on the stationary portion 46.

The stationary portion 46 may, if desired, include a thumb ring 50 while the movable portion 48 includes one or more finger rings 52. Thus, a physician or other professional may activate the sphincterotome 10 by holding the thumb ring 50 in his or her thumb and using their fingers to pull the finger rings 52 (and thus the movable portion 48) proximally.

The handle 16 may also, if desired, include a connector block 80 that may be used to provide communication between the cutting element 40 and a RF heating source, as is known in the art, in order to energize the cutting element 40.

The distal region 20 of the elongate shaft 18 may, as illustrated, include one or more marker bands 54. The marker bands 54, if present, may be formed of any suitable radiopaque material and may have any appropriate dimensions and/or axial spacing, as desired. In some cases, the marker bands 54 may be visually evident during use, and therefore in some instances, the marker bands 54 may not be formed of a radiopaque material but may instead simply be applied using a material of a different color. The marker bands 54 may aid in positioning the sphincterotome 10 during a procedure.

The distal region 20 of the elongate shaft 18 also includes elements not expressly illustrated in FIG. 1. In particular, FIG. 4 provides a view of a micromachined hypotube 56 that may be disposed within or about at least a portion of the distal region 20 of the elongate shaft 18. The micromachined hypotube 56 has a proximal portion 58 defining a proximal end 60 and a distal region 62 defining a distal end 64. The micromachined hypotube 56 has a first side 66 and a second side 68. The first side 66 may include a first plurality of slots 70 while the second side 68 includes a second plurality of slots 72. At least some of the first plurality of slots 70 may be parallel. At least some of the second plurality of slots 72 may be parallel.

Each of the first plurality of slots 70 and each of the second plurality of slots 72 extend only partially around the circumference of the micromachined hypotube 56. In some instances, as illustrated, each of the first plurality of slots 70 and each of the second plurality of slots 72 are at least substantially equally sized in length and width, and start and stop along common lines. While not illustrated, it is contemplated that the relative axial spacing and/or width of some of the slots within the first plurality of slots 70 and/or the second plurality of slots 72 may vary in order to provide customized flexibility control.

It can be seen that the micromachined hypotube 56 will have a greater flexibility in a first bending plane in which, for example, at least some of the first plurality of slots 70 open while at least some of the second plurality of slots 72 close. Conversely, the micromachined hypotube 56 will have a reduced flexibility in a second bending plane that is orthogonal to the first bending plane. It can be seen that the first bending plane may be referred to as an activating bending plane while the second bending plane might be referred to as an orthogonal bending plane.

Each slot within the first plurality of slots 68 and the second plurality of slots may be formed to be at least largely rectangular in shape. In some instances, at least some of the slots may not extend all the way through micromachined hypotube 56. Each slot may be formed using any suitable technique, such as saw cutting, a laser, or even by electrical discharge machining (EDM). Additional suitable techniques include chemical etching and abrasive grinding.

The micromachined hypotube 56 may be formed of any suitable polymeric or metallic material. In some cases, the micromachined hypotube 56 may be formed of a suitably stiff polymer such as carbon fibers, liquid crystal polymers, polyimide, and the like. In some instances, the micromachined hypotube 56 may be formed of a metallic material such as stainless steel or a nickel-titanium alloy such as Nitinol or other metallic or polymeric shape-memory material. The micromachined hypotube 56 may include a combination of metal tubes and polymer tubes, if desired. In some cases, the micromachined hypotube 56 may be formed as an integral part of the elongate shaft 18, or in some instances, the slots may instead be formed within the elongate shaft 18 itself.

The micromachined hypotube 56 may be formed having any desired length, width, material thickness, and slot size as required to satisfy the requirements of any particular application. Additional details concerning micromachined hypotube 56, including the manufacture thereof, can be found, for example, in U.S. Pat. No. 6,766,720 and U.S. Patent Publication No. 2004/0181174A2, each of which are incorporated by reference herein to the extent that they do not conflict with the present disclosure.

Figure 5:
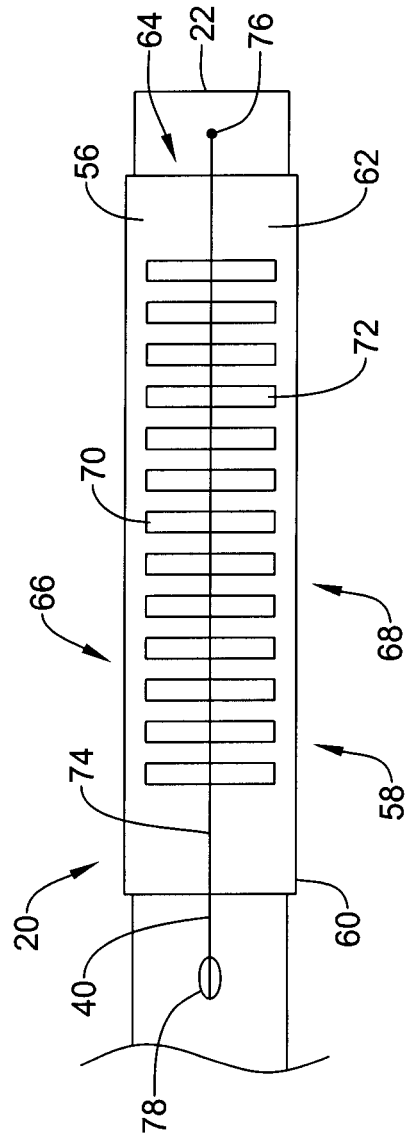
FIG. 5 is a top view of a distal portion of the sphincterotome of FIG. 1, incorporating the micromachined hypotube of FIG. 4 in accordance with an illustrative but non-limiting example of the invention.
Figure 6:
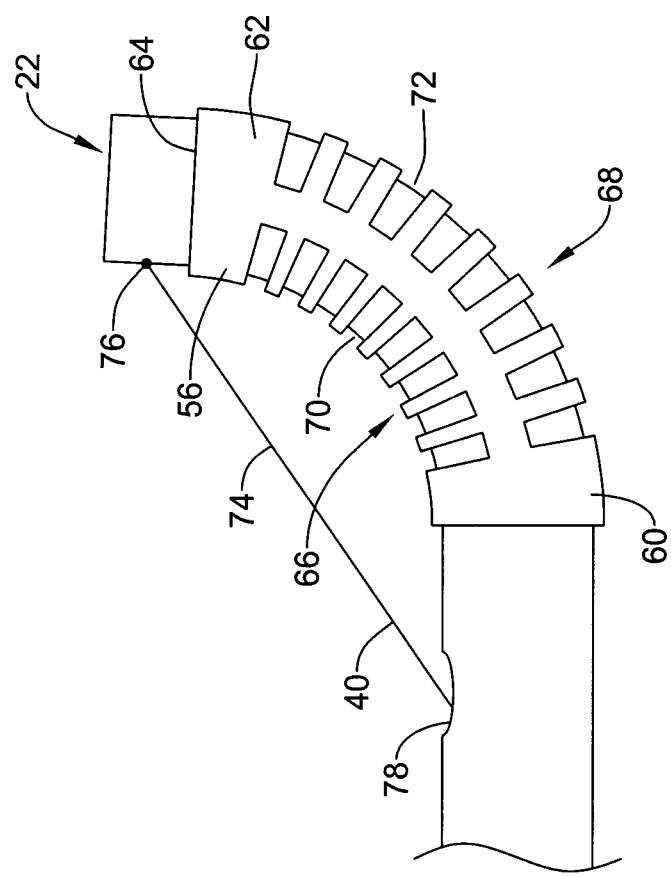
FIG. 6 is a side view of a distal portion of the sphincterotome of FIG. 1, incorporating the micromachined hypotube of FIG. 4 in accordance with an illustrative but non-limiting example of the invention, shown in a curved configuration.

FIGS. 5 and 6 clarify operation of the sphincterotome 10. In FIG. 5, the micromachined hypotube 56 has been disposed about or within the distal region 20 of the elongate shaft 18. In some cases, the micromachined hypotube 56 may be disposed about an exterior of the elongate shaft 18. If desired, and to electrically isolate the micromachined hypotube 56 from the cutting element 40, a polymeric coating or sheath may be applied to the micromachined hypotube 56. In some instances, the micromachined hypotube 56 may be molded within the polymeric or other material forming the elongate shaft 18, as desired.

The cutting element 40 includes an exposed cutting portion 74 that extends from a distal end 76 of the cutting element 40 to a port 78 disposed within the elongate shaft 18. As illustrated, the distal end 76 of the cutting element 40 is secured directly to the distal region 62 of the micromachined hypotube 56. In some cases, it is contemplated that the cutting element 40 could instead pass through an aperture (not illustrated) or rest within a slot or channel within the micromachined hypotube 56 such that the distal end 76 of the cutting element 40 could instead be anchored directly to the elongate shaft 18.

As noted previously, the cutting element 40 extends proximally to the handle 16. The port 78 is an aperture formed within the wall of the elongate shaft 18 and may, if desired, include reinforcing structure (not illustrated). In FIG. 5, the exposed cutting portion 74 can be seen to be in a non-cutting position in which the exposed cutting portion 74 of the cutting element 40 is at least substantially parallel with the elongate shaft 18.

In FIG. 6, however, the exposed cutting portion 74 of the cutting element 40 is in a cutting position in which the exposed cutting portion 74 of the cutting element 40 has pulled away from the elongate shaft 18 as a result of proximal movement of the movable portion 48 relative to the stationary portion 46. It can be seen that the micromachined hypotube 56 provides at least part of the distal region 20 with a smooth curvature that is free of kinks.

As discussed above, the micromachined hypotube 56 is configured to be more flexible in a first bending plane and less flexible in a second, orthogonal bending plane. The micromachined hypotube 56 may be secured to the elongate shaft 18 oriented in such a way that when a tensile force is applied to the cutting element 40, the first bending plane corresponds to the "12 o'clock" direction. As a result, the sphincterotome 10 will reliably or predictably bend in a desired direction.

In some instances, it is contemplated that the cutting element 40 may not actuate in exactly a desired direction or plane. This may occur, for example, as a result of manufacturing tolerances, interference from the anatomy, influence from an endoscope, and the like. Nevertheless, the sphincterotome 10 will, as a result of micromachined hypotube 56, reliably and repeatedly bend in a desired plane.

The devices described herein may include a variety of different materials. These materials may include metals, metal alloys, polymers, metal-polymer composite, and the like, or any other suitable material. Some examples of suitable metals and metal alloys include stainless steel, such as 304V, 304L, and 316LV stainless steel; mild steel; nickel-titanium alloy such as linear-elastic or super-elastic nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; other Co—Cr alloys; platinum enriched stainless steel; or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly (alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

In addition, the devices described herein may also be doped with or otherwise include a radiopaque material. Radiopaque materials are understood to be materials capable of producing a relatively bright image on a fluoroscopy screen or another imaging technique during a medical procedure. This relatively bright image aids the user of filtering device in determining their location. Some examples of radiopaque materials can include, but are not limited to, gold, platinum, molybdenum, palladium, tantalum, tungsten or tungsten alloy, plastic material loaded with a radiopaque filler, and the like.

The invention should not be considered limited to the particular examples described above, but rather should be understood to cover all aspects of the invention as set out in the attached claims. Various modifications, equivalent processes, as well as numerous structures to which the invention can be applicable will be readily apparent to those of skill in the art upon review of the instant specification.

I claim:

1. A sphincterotome, comprising:
   an elongate shaft defining a cutting wire lumen;
   a cutting wire disposed within the cutting wire lumen; and
   a bending plane controlling structure disposed exterior to the elongate shaft, the bending plane controlling structure including a tubular member having a plurality of slots formed therein, the tubular member having a first side and a second side opposite the first side, wherein the plurality of slots are formed in only the first and second sides, wherein the tubular member resists bending of the shaft in directions orthogonal to the first and second sides;
   wherein the sphincterotome is movable between a cutting position and a non-cutting position.

2. The sphincterotome of claim 1, wherein the bending plane controlling structure provides a directed bending plane when the sphincterotome is activated into the cutting position.

3. The sphincterotome of claim 1, wherein the bending plane controlling structure provides a smooth curvature to a distal portion of the elongate shaft when the sphincterotome is activated into the cutting position.

4. A sphincterotome, comprising:
   an elongate shaft having a lumen formed therein and having a distal end;
   wherein a distal port is formed in the shaft;
   wherein the distal port is positioned proximal of the distal end of the shaft;
   a cutting wire extending through the lumen; and
   a tubular member coupled to the shaft, the tubular member having a plurality of slots formed therein, the plurality of slots being formed only on two opposite sides of the tubular member, wherein the tubular member resists bending of the shaft in directions orthogonal to the two opposite sides;
   wherein the cutting wire extends through the distal port and along a portion of an outer surface of the tubular member.

5. The sphincterotome of claim 4, wherein a first group of parallel slots extend along a first side of the tubular member.

6. The sphincterotome of claim 5, wherein the cutting wire extends along the first side of the tubular member.

7. The sphincterotome of claim 5, wherein the first side of the tubular member defines a first preferred bending direction for the shaft.

8. The sphincterotome of claim 7, wherein a second group of parallel slots extend along a second side of the tubular member, the second side being opposite the first side.

9. The sphincterotome of claim 8, wherein the second side of the tubular member defines a second preferred bending direction for the shaft.

10. The sphincterotome of claim 9, wherein the tubular member resists bending of the shaft in directions orthogonal to the first preferred bending direction and the second preferred bending direction.

* * * * *